United States Patent [19]
Preston

[11] Patent Number: 5,663,454
[45] Date of Patent: Sep. 2, 1997

[54] METHOD FOR THE MANUFACTURE AND PURIFICATION OF METHYL TERTIARY BUTYL ETHER AND DIMETHYL ETHER

[75] Inventor: Kyle Lee Preston, Port Arthur, Tex.

[73] Assignee: Huntsman Specialty Chemicals Corporation, Salt Lake City, Utah

[21] Appl. No.: 512,723

[22] Filed: Aug. 8, 1995

[51] Int. Cl.$^6$ .................................................. C07C 41/06
[52] U.S. Cl. .......................... 568/697; 568/698; 568/699
[58] Field of Search .................................. 568/697, 698, 568/699

[56] References Cited

U.S. PATENT DOCUMENTS

| | | | |
|---|---|---|---|
| 5,243,091 | 9/1993 | Kruse et al. | 568/697 |
| 5,292,964 | 3/1994 | Gupta et al. | 568/697 |
| 5,320,051 | 6/1994 | Eason et al. | 568/699 |
| 5,354,912 | 10/1994 | Hwan et al. | 568/697 |

*Primary Examiner*—C. Warren Ivy
*Assistant Examiner*—Sreeni Padmanabhan
*Attorney, Agent, or Firm*—Russell R. Stolle; Carl G. Ries

[57] ABSTRACT

Methanol and isobutylene are reacted to form a methyl tertiary butyl ether product stream containing contaminating quantities of dimethyl ether, methanol and isobutylene that is separated into a first fraction comprising isobutylene and methyl tertiary butyl ether and a second fraction comprising residual methyl tertiary butyl ether, methanol, dimethyl ether and water. The second fraction is separated into a first lower boiling distillation fraction comprising methyl tertiary butyl ether, methanol, isobutylene, dimethyl ether, and water and a first higher boiling distillation fraction comprising methanol and water. Dimethyl ether and isobutylene are recovered from the first lower boiling distillation fraction and charged to a second distillation column for separation into a second lower boiling distillation fraction consisting essentially of dimethyl ether and a second higher boiling distillation fraction comprising dimethyl ether and isobutylene.

3 Claims, 1 Drawing Sheet

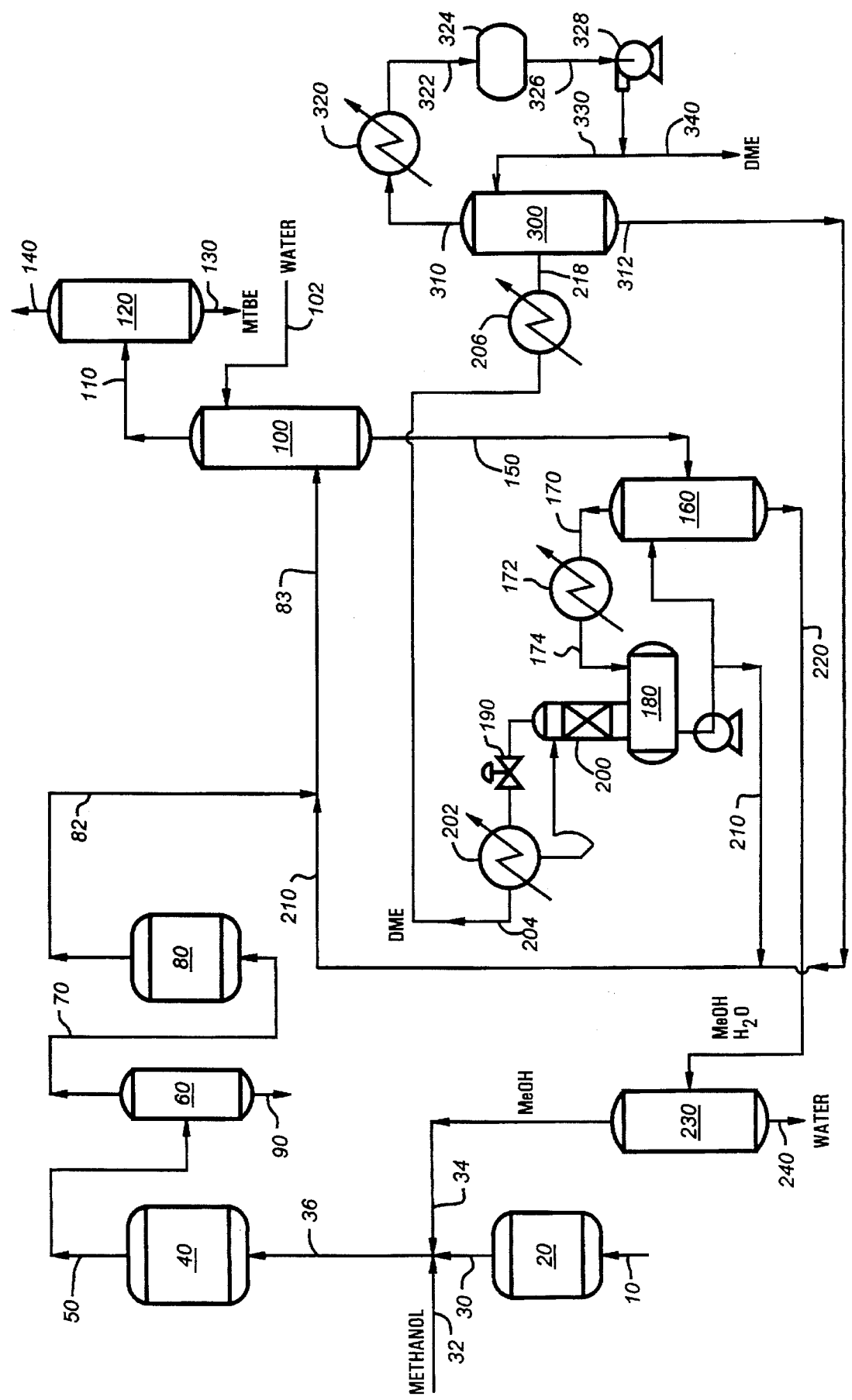

METHOD FOR THE MANUFACTURE AND PURIFICATION OF METHYL TERTIARY BUTYL ETHER AND DIMETHYL ETHER

BACKGROUND OF THE INVENTION

1. Technical Field of the Invention

This invention relates to a method for the recovery of dimethyl ether formed during the manufacture of methyl tertiary butyl ether. This invention more particularly relates to a method for the manufacture and purification of methyl tertiary butyl ether and dimethyl ether. Still more particularly, this invention relates to a method for the manufacture of methyl tertiary butyl ether and dimethyl ether from tertiary butyl alcohol, isobutylene and methanol and for the separate purification of the methyl tertiary butyl ether and dimethyl ether formed by the reaction. In particular, this invention relates to a method for the manufacture of methyl tertiary butyl ether and dimethyl ether from tertiary butyl alcohol, isobutylene and methanol and for an improvement in the separate purification of the methyl tertiary butyl ether and dimethyl ether formed during the reaction.

2. Prior Art

The preparation of methyl tert-butyl ether from methyl and tert-butyl alcohols is discussed in S. V. Rozhkov et al., Prevrashch Uglevodorodov, Kislotno-Osnovn. Geterogennykh Katal. Tezisy Dokl., Vses. Konf., 1977, 150 (C. A. 92:58165y). Here the TBA and methanol undergo etherification over KU-2 strongly acidic sulfopolystyrene cation-exchangers under mild conditions. This reference contains data on basic parameters of such a process.

In U.S. Pat. No. 5,354,912 a process is provided wherein by-product isobutylene formed when methanol is reacted with tertiary butyl alcohol is further reacted downstream of the tertiary butyl alcohol etherification reaction zone with methanol to form a reaction product comprising methyl tertiary butyl ether and dimethyl ether and wherein the methyl tertiary butyl ether formed by the reactions is purified by the removal of impurities, including di-methyl ether.

In U.S. Pat. No. 4,144,138 (1979) to Rao et al., there is disclosed a method for recovering methyl tertiary butyl ether from an etherification reaction effluent by azeotropic distillation to recover a methanol-ether azeotrope overhead which is water-washed to give pure ether raffinate, the latter being azeotropically distilled to yield ether-methanol overhead which is recycled to water washing.

Kruse et al. U.S. Pat. No. 5,243,091, entitled "Method for the Manufacture and Recovery of Methyl Tertiary Butyl Ether", discloses a method for the preparation of methyl tertiary butyl ether wherein tertiary butyl alcohol is reacted with methanol to provide a reaction product comprising methyl tertiary butyl ether and by-product isobutylene and wherein the by-product isobutylene is reacted with methanol to provide additional methyl tertiary butyl ether and also a method for the purification of the methyl tertiary butyl ether.

Gupta U.S. Pat. No. 5,292,964 discloses a process for the manufacture of methyl tertiary butyl ether from tertiary butyl alcohol and methanol wherein tertiary butyl alcohol is reacted with methanol in a primary reaction zone to provide a reaction product comprising methyl tertiary butyl ether, unreacted tertiary butyl alcohol, unreacted methanol and water, wherein the reaction product is separated in a distillation zone into a lighter fraction comprising substantially anhydrous methanol and methyl tertiary butyl alcohol and a heavier fraction comprising tertiary butyl alcohol, methanol and water, and wherein the lighter fraction is charged to a finishing reactor wherein the methanol is reacted with isobutylene to form additional methyl tertiary butyl ether.

Trubac U.S. Pat. No. 4,814,517 discloses a modified method for the purification of methyl tertiary butyl ether manufactured from methanol and isobutylene wherein a distillate overhead stream obtained during the purification of the methyl tertiary butyl ether is passed in liquid phase sequentially through a bed of silica gel to removal methanol and a bed of a zeolite molecular sieve to remove dimethyl ether.

BACKGROUND INFORMATION

Methyl tertiary butyl ether (MTBE) is finding increasing use as a blending component in high octane gasoline as the current gasoline additives based on lead and manganese are phased out.

Dimethyl ether (DME) is finding increasing use as a replacement for Freon-type chemicals; for example, for use as a propellant.

With the expanding use of MTBE as an acceptable gasoline additive, a growing problem is the availability of raw materials. Historically, the critical raw material is isobutylene (Oil and Gas J., Jun. 8, 1987, p. 55). It would be advantageous, therefore, to have a process to make MTBE that does not require isobutylene as a building block. It would be advantageous to have an efficient process for making MTBE by reaction of methanol with tertiary butyl alcohol, since tertiary butyl alcohol (TBA) is readily available commercially through isobutane oxidation.

It is known to react methanol with tertiary butyl alcohol in the presence of a catalyst in order to produce methyl tertiary butyl ether. A wide variety of catalysts have been suggested for this purpose.

In U.S. Pat. No. 2,282,469 to Frolich there is disclosed a process for preparing methyl tertiary butyl ether over a catalyst comprising Kieselguhr impregnated with phosphoric acid at a temperature of about 175° F. to 350° F.

Japanese Patent 0007432 teaches the use of zeolites to make dialkyl ethers containing primary or secondary alkyl groups. The zeolites have a porous structure and are represented by:

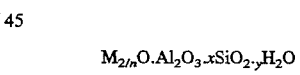

where M is an alkali metal or alkaline earth metal cation or organic base cation, n is the valence of the cation and x and y are variables.

U.S. Pat. No. 4,058,576 to Chang et al. teaches the use of (pentasil-type) aluminosilicate zeolites, such as ZSM-5, having a pore size greater than 5 angstrom units and a silica-to-alumina ratio of at least 12, to convert lower alcohols to a mixture of ethers and olefins.

In U.S. Pat. No. 4,822,921 there is disclosed a method for producing MTBE by reacting tertiary butyl alcohol and methanol in the presence of a catalyst comprising an inert support, such as titania, having a phosphoric acid impregnated thereon.

U.S. Pat. No. 4,827,048 discloses a method for producing MTBE by reacting tertiary butyl alcohol and methanol in the presence of a catalyst comprising a heteropoly acid such as 12-tungstophosphoric acid or 12-molybdophosphoric acid on an inert support, such as titania.

Among the by-products formed during the reaction of the methanol with tertiary butyl alcohol are water and isobutylene. When the isobutylene is reacted with methanol to form additional methyl tertiary butyl ether, dimethyl ether is formed as a by-product.

SUMMARY OF THE INVENTION

1

In accordance with the present invention, an improved method for obtaining high purity dimethyl ether is provided wherein methanol and isobutylene are reacted in the presence of a solid etherification catalyst to form a methyl tertiary butyl ether product stream containing contaminating quantities of water, dimethyl ether, methanol and isobutylene, the improved method comprising the steps of:

a) separating the methyl tertiary butyl ether product stream into a first fraction comprising isobutylene and methyl tertiary butyl ether and a second fraction comprising residual methyl tertiary butyl ether, methanol, dimethyl ether and water, b) charging the second fraction to a dimethyl ether recovery distillation column and separating it therein into a first lower boiling (lighter) distillation fraction comprising methyl tertiary butyl ether, methanol, isobutylene, dimethyl ether, and water and a first higher boiling (heavier) distillation fraction comprising methanol and water, c) recovering dimethyl ether and isobutylene from the first lower boiling (lighter) distillation fraction, and d) charging the recovered dimethyl ether and isobutylene to a dimethyl ether purification distillation column and separating it therein into a second lower boiling (lighter) distillation fraction consisting essentially of dimethyl ether and a second higher boiling (heavier) distillation fraction comprising dimethyl ether and isobutylene.

2

In accordance with a more preferred embodiment of the present invention, an improved method for obtaining high purity dimethyl ether is provided wherein methanol and isobutylene are reacted in the presence of a solid etherification catalyst to form a methyl tertiary butyl ether product stream containing contaminating quantities of water, dimethyl ether, methanol and isobutylene, the improved method comprising the steps of:

a) continuously charging the methyl tertiary butyl ether product stream to a methanol solvent extraction zone and countercurrently contacting it therein with water to provide an extract comprising isobutylene and methyl tertiary butyl ether and a bottoms raffinate comprising residual methyl tertiary butyl ether, methanol, dimethyl ether and water, b) charging the raffinate to a dimethyl ether recovery distillation column and separating it therein into a lower boiling (lighter) distillation fraction comprising methyl tertiary butyl ether, methanol, isobutylene, dimethyl ether, and water and a higher boiling (heavier) distillation fraction comprising methanol and water, c) charging the lower boiling (lighter) distillation fraction, as a liquid, to an accumulator and venting from the drum a vapor by-product comprising dimethyl ether and isobutylene, d) liquefying the vented dimethyl ether and isobutylene, and e) charging the liquified dimethyl ether and isobutylene to a dimethyl ether purification distillation column and separating it therein into a lower boiling (lighter) distillation fraction consisting essentially of dimethyl ether and a higher boiling (heavier) distillation fraction comprising dimethyl ether and isobutylene.

3

In accordance with another preferred embodiment of the present invention, a process for producing dimethyl ether and methyl tertiary butyl ether is provided comprising the steps of:

a) continuously reacting methanol with tertiary butyl alcohol in a tertiary butyl alcohol etherification reaction zone containing a bed of an etherification catalyst to form a tertiary butyl alcohol reaction product comprising methanol, unreacted tertiary butyl alcohol, water, isobutylene and methyl tertiary butyl ether, b) continuously charging the tertiary butyl alcohol reaction product to a primary methyl tertiary butyl ether recovery distillation zone and separating it therein into a first lower boiling (lighter) distillation fraction comprising methyl tertiary butyl ether, isobutylene and methanol and a first higher boiling (heavier) distillation fraction comprising methanol, tertiary butyl alcohol and water, c) continuously charging the first lower boiling (lighter) distillation fraction to an isobutylene conversion reaction zone and contacting it therein with a solid resin etherification catalyst to thereby convert isobutylene and methanol to methyl tertiary butyl ether and form a methyl tertiary butyl ether product stream containing contaminating quantities of dimethyl ether, methanol and isobutylene, d) continuously charging the methyl tertiary butyl ether product stream to a methanol solvent extraction zone and countercurrently contacting it therein with water to provide an extract comprising isobutylene and methyl tertiary butyl ether and a bottoms raffinate comprising residual methyl tertiary butyl ether, methanol, dimethyl ether and water, e) continuously charging the extract to a methyl tertiary butyl ether purification distillation zone and separating it therein into a second lower boiling (lighter) distillation fraction comprising isobutylene and water and into a second higher boiling (heavier) distillation fraction consisting essentially of methyl tertiary butyl ether, f) continuously charging the raffinate to a dimethyl ether recovery distillation zone and separating it therein into a third lower boiling (lighter) distillation fraction comprising methyl tertiary butyl ether, methanol, isobutylene, dimethyl ether and water and a third higher boiling (heavier) distillation fraction comprising methanol and water, g) continuously charging the third lower boiling (lighter) distillation fraction, as a liquid, to a drum and venting from the drum a vapor by-product comprising dimethyl ether, and isobutylene, h) liquefying the vented dimethyl ether and isobutylene, and i) charging the liquified dimethyl ether and isobutylene to a dimethyl ether purification distillation column and separating it therein into a fourth lower boiling (lighter) distillation fraction consisting essentially of dimethyl ether and a fourth higher boiling (heavier) distillation fraction comprising dimethyl ether and isobutylene.

The Tertiary Butyl Alcohol Feedstock

Tertiary butyl alcohol can be produced by the thermal or catalytic decomposition of tertiary butyl hydroperoxide. Tertiary butyl alcohol formed in this fashion will normally contain a minor amount of peroxide contaminants such as tertiary butyl hydroperoxide, ditertiarybutyl peroxide, allyl tertiary butyl peroxide, etc. Normally, the peroxide contaminants in the tertiary butyl alcohol will remain as contaminants in the etherification reaction zone reaction product.

The peroxides-contaminated tertiary butyl alcohol may be charged to a peroxide decomposition reaction zone where the peroxide contaminants are thermally or catalytically decomposed to form a tertiary butyl alcohol feedstock that is substantially completely free from peroxide contaminants. Contaminating quantities of decomposition products such as acetone and methyl formate will normally be present.

When the peroxides are to be thermally decomposed, the peroxides-contaminated tertiary butyl alcohol feedstock is passed through a peroxides decomposition reactor under decomposition conditions including a temperature of about 100° to about 200° C., a pressure of about 80 to about 500 psia and a flow rate of about 0.5 to about 20 volumes of feedstock per reactor volume per hour to thereby provide a substantially peroxides-free tertiary butyl alcohol reaction product. Alternately, the peroxide contaminants may be catalytically decomposed.

A wide variety of catalysts may be used for this purpose, such as cobalt borate as disclosed in U.S. Pat. No. 4,547,598, a nickel, copper, chromia catalyst as disclosed in Sanderson et al. U.S. Pat. No. 4,704,482, an iron, copper, chromia, cobalt catalyst as disclosed in Sanderson et al. U.S. Pat. No. 4,705,903, a base treated hydrogenation catalyst from groups VIB or VIIIB of the Periodic Table as disclosed in Sanderson et al. U.S. Pat. No. 4,742,179, a nickel, copper, chromium and barium catalyst as disclosed in Sanderson et al. U.S. Pat. No. 4,873,380, a metal phthalocyanine catalyst as disclosed in Sanderson et al. U.S. Pat. No. 4,910,349, an imidazole-promoted methyl metal phthalocyanine catalyst as disclosed in Sanderson et al. U.S. Pat. No. 4,912,266, a base promoted metal phthalocyanine catalyst as disclosed in Sanderson et al. U.S. Pat. No. 4,912,267, a solid ruthenium catalyst as disclosed in Sanderson et al. U.S. Pat. No. 4,922,033, a promoted metal porphine catalyst as disclosed in Sanderson et al. U.S. Pat. No. 4,922,034, etc.

DETAILED DESCRIPTION OF THE PRESENT INVENTION

The Tertiary Butyl Alcohol Etherification Reaction Catalyst

In accordance with the method of the present invention, a tertiary butyl alcohol etherification reaction zone containing a bed of etherification catalyst is utilized. A wide variety of etherification catalysts can be used for this purpose, such as Kieselguhr impregnated with phosphoric acid as disclosed in Frolich U.S. Pat. No. 2,282,469, zeolites as disclosed in Japanese Patent 0007432, aluminosilicate zeolites as disclosed in Chang et al. U.S. Pat. No. 4,058,576, titania having phosphoric acid impregnated thereon as disclosed in Knifton U.S. Pat. No. 4,822,921, a hetero polyacid such as 12-tungstophosphoric acid or 12-molybdophosphoric acid supported on titania, etc.

A preferred catalyst is a strongly acidic ion exchange resin consisting essentially of sulfonated polystyrene, such as a divinyl benzene crosslinked polystyrene matrix containing from about 0.5 to about 20% of copolymerized divinyl benzene. Resins of this nature are manufactured and sold commercially under various trade names such as "Dowex 50", "Nalcite HCR" and "Amberlyst 15". The use of catalysts of this nature is disclosed, for example, in Rao U.S. Pat. No. 4,144,138.

The reaction conditions to be utilized when reacting methanol with tertiary butyl alcohol in the presence of an etherification catalyst of the type disclosed include a reaction temperature of about 90° to about 140° C., a pressure of about 30 to about 500 psia and a space velocity of about 0.5 to about 20 volumes of feed per volume of etherification catalyst per hour.

The Solid Resin Etherification Catalyst

In accordance with the present invention, a distillate fraction is obtained during the recovery process which contains isobutylene, methanol and methyl tertiary butyl ether and it is brought into contact with a solid resin isobutylene etherification catalyst in order to convert a significant portion of the isobutylene and methanol to methyl tertiary butyl ether.

Any suitable solid resin etherification catalyst may be used for this purpose, such as a strongly acidic ion exchange resin consisting essentially of sulfonated polystyrene, such as a divinyl benzene crosslinked polystyrene matrix containing from about 0.5 to about 20% of copolymerized divinyl benzene. Resins of this nature are manufactured and sold commercially under various trade names such as "Dowex 50", "Nalcite HCR" and "Amberlyst 15".

The methanol and isobutylene-containing methyl tertiary butyl ether distillation fraction will normally contain from about 5 to about 10 wt. % of isobutylene, and from about 70 to about 80 wt. % of methyl tertiary butyl ether and from about 10 to about 20 wt. % of methanol. The feedstock for the isobutylene conversion reaction zone may comprise the methanol and isobutylene-containing methyl tertiary butyl ether distillation fraction which may be used alone, or in admixture with additional isobutylene added from another source (e.g., isobutylene recovered from the third lower boiling (lighter) distillation fraction).

The methanol and isobutylene-containing methyl tertiary butyl ether distillation fraction, or isobutylene feedstock is brought into contact with a solid resin isobutylene etherification catalyst in the isobutylene conversion reaction zone under conversion conditions including, for example, a temperature of about 35° to about 130° C., a pressure of about 30 to about 500 psia and a space velocity of about 0.5 to about 20 volumes of feedstock per volume of etherification catalyst per hour. As a consequence, an isobutylene conversion product is formed which will normally contain from about 0 to about 10 wt. % of isobutylene, about 75 to about 85 wt. % of methyl tertiary butyl ether and from about 10 to about 15 wt. % of methanol. The isobutylene conversion product will also contain contaminating quantities of dimethyl ether (e.g., from about 0.5 to about 5.0 wt. % of dimethyl ether.

BRIEF DESCRIPTION OF THE DRAWING

The drawing is a schematic flow sheet with conventional parts omitted showing the general reaction and recovery sequence of the present invention for the manufacture and purification of methyl tertiary butyl ether and dimethyl ether.

DESCRIPTION OF THE PREFERRED EMBODIMENT

Turning now to the drawing, there is shown a schematic flow sheet illustrating the preferred method for the practice of the process of the present invention. In the drawing, conventional parts, such as valves, pumps, temperature control sensors, pressure sensors, heaters, coolers, flow control regulation apparatus, reflux condenses, reboilers, etc., have been omitted.

In accordance with a preferred embodiment of the present invention, a peroxides-contaminated, or "crude" tertiary butyl alcohol feed is charged by way of line 10 to a peroxide decomposition reaction zone 20 where thermal peroxide decomposition conditions are established, including a temperature of about 100° to about 200° C., a pressure of about 80 to about 500 psia and a flow rate of about 0.5 to about 20 volumes of feedstock per reactor volume per hour to thereby provide a substantially peroxides-free tertiary butyl alcohol reaction product that is discharged from the peroxide decomposition zone 20 by a discharge line 30.

The peroxides-free decomposition reaction product discharged from the peroxide decomposition zone 20 will typically have a composition as follows:

TABLE 1

PEROXIDE REACTION ZONE DECOMPOSITION PRODUCT

| Component | % |
|---|---|
| TBA[1] | 97.4 |
| Water | 0.02 |
| Other[2] | 2.6 |

[1]Tertiary butyl alcohol
[2]Acetone, tertiary butyl formate, isopropyl alcohol, etc.

In accordance with the present invention, there is provided an etherification reaction zone 40 containing a bed of a solid etherification catalyst. A preferred catalyst is a sulfonic acid resin etherification catalyst such as a sulfonated polystyrene resin cross-linked with divinyl benzene (e.g., a strongly acidic ion exchange resin consisting essentially of sulfonated polystyrene, such as a divinyl benzene crosslinked polystyrene matrix containing from about 0.5 to about 20% of copolymerized divinyl benzene, such as a strongly acidic ion exchange resin manufactured and sold commercially under the trade name "Dowex 50", "Nalcite HCR" or "Amberlyst 15").

Alternately, other catalysts known to those skilled in the art may be used, such as a fluorophosphoric acid-on-titania catalyst prepared in the manner described in Knifton et al. U.S. Pat. No. 4,822,921 by treating titania extrudates, such as extrudates having a surface area of about 50 m2/g, with an acetone solution of fluorophosphoric acid to provide as a catalyst, titania having about 3.0 wt. % of phosphorus and about 0.6 wt. % of fluorine deposited thereon and bonded thereto by a calcining treatment.

A tertiary butyl alcohol feed mixture is charged to the etherification reaction zone 40 by the line 36; the feed mixture 36 comprising substantially peroxides-free tertiary butyl alcohol charged by the line 30, fresh methanol charged by the line 32 and recycle methanol charged by a recycle line 34. Methanol is charged to the feed line 36 through methanol charge lines 32 and 34 in an amount such that the molar ratio of methanol to tertiary butyl alcohol is within the range of about 1.1 to about 4:1 and, more preferably, from about 1.5 to about 2.5:1 and, still more preferably, in the ratio of about 2 moles of methanol per mole of tertiary butyl alcohol. It will be understood that tertiary butyl alcohol prepared by the thermal or catalytic decomposition of tertiary butyl hydroperoxide will contain minor amounts of impurities such that, for example, the feedstock charged to the reaction 40 through the feed line 36 will contain the following components:

TABLE 2

ETHERIFICATION REACTION ZONE FEED MIXTURE

| Component | % |
|---|---|
| Methanol | 40.0 |
| TBA[1] | 46.7 |
| Acetone | 0.5 |
| 2-Propanol | 1.1 |
| MTBE[2] | 2.0 |
| DTBP[3] | 4.5 |
| t-Butyl Formate | 0.2 |
| Water | 5.0 |

[1]Tertiary butyl alcohol
[2]Methyl tertiary butyl ether
[3]Ditertiary butyl peroxide It will be understood that trace amounts of other peroxides such as tertiary butyl hydroperoxide, tertiary allyl peroxide, etc., may also be present.

Within the etherification reaction zone 40, the tertiary butyl alcohol feed mixture is brought into contact with the bed of etherification catalyst under reaction conditions including a temperature of about 30° C. to about 200° C., and more preferably from about 80° to about 140° C., and still more preferably from about 90° to about 130° C. and a pressure of about 30 to about 500 psia, and more preferably from about 200 to about 300 psia. Space velocities within the etherification reaction zone are suitably such that about 0.5 to about 20 volumes of feed mixture per volume of etherification catalyst per hour are fed to the etherification reaction zone 10 and, more preferably from about 1 to about 4 volumes of feed mixture per volume of etherification catalyst per hour.

Within the etherification reaction zone 40, methanol will exothermally react with the tertiary butyl alcohol to form methyl tertiary butyl ether which will be contained in a tertiary butyl alcohol reaction product discharged from the etherification reaction zone 40 by way of a line 50 leading to a primary methyl tertiary butyl ether (MTBE) distillation zone 60.

As a specific example, when the solid etherification catalyst is a sulfonic acid resin such as Amberlyst 15 and when the molar ratio of methanol to tertiary butyl alcohol in the feed mixture charged to the etherification reaction zone 40 by the line 36 is about 2 moles of methanol per mole of tertiary butyl alcohol, and the reaction is conducted at a temperature of about 100° C. at a feed rate of about 2 volumes of feed mixture per volume of catalyst per hour, the etherification reaction product may have the composition shown by the following table:

TABLE 3

ETHERIFICATION REACTION PRODUCT

| Component | % |
|---|---|
| Water | 14.0 |
| Methanol | 27.8 |
| Isobutylene | 3.0 |
| TBA[1] | 14.1 |
| MTBE[2] | 34.5 |
| Other[3] | 6.8 |

[1]Tertiary butyl alcohol
[2]Methyl tertiary butyl ether
[3]Includes the acetone, propanol, ditertiary butyl peroxide, tertiary butyl formate, etc., initially present in the tertiary butyl alcohol feedstock.

The tertiary butyl alcohol etherification reaction product charged to the primary distillation zone 60 by way the charge line 50 is fractionated therein under distillation conditions including a liquid reflux temperature of about 30° to about 100° C., and more preferably about 40° to about 80° C., a reboiler temperature of about 80° to about 115° C., and more preferably from about 95° to about 105° C., and a pressure of about 15 to about 60 psia, the distillation condition being selected such that substantially all of the MTBE in the etherification reaction product 50 is taken overhead from the primary distillation zone 60 by a line 70. As a consequence, the first distillation fraction 70 taken overhead from the distillation zone 60 will comprise substantially all of the isobutylene and substantially all of the methyl tertiary butyl ether and some of the methanol charged to the first distillation zone 60. The second higher boiling (heavier) distillation fraction 90 discharged from the first MTBE distillation zone 60 will comprise methanol, tertiary butyl alcohol and water.

In accordance with the present invention, methanol and isobutylene-containing methyl tertiary butyl ether distillation fraction 70 is charged to an isobutylene conversion zone 80 containing a bed of solid resin etherification catalyst such as a bed of Amberlyst 15 sulfonated polystyrene-divinyl benzene copolymer acidic ion exchange resin. If desired, additional isobutylene may be charged to the isobutylene conversion zone 80 from a suitable source, not shown, such as isobutylene recovered from the distillate fraction 140, which is obtained in a manner to be described; the additional isobutylene comprising about 2 to 15 wt. % of the weight of the first distillation fraction 70.

Etherification reaction conditions established in the isobutylene conversion zone 80 include, for example, a temperature of about 35° to about 130° C., and more preferably from about 40° to about 70° C., a pressure of about 50 to about 500 psia, and more preferably from about 150 to about 250 psia, and a space velocity of about 0.5 to about 4 volumes of isobutylene feed mixture per volume of solid resin etherification catalyst per hour. As a consequence, a portion of the methanol and isobutylene contained in the primary distillation fraction 50 will be converted to methyl tertiary butyl ether. Typically, the conversion will amount to about 30 to about 40 wt. %, based on the isobutylene. By-product dimethyl ether will also be formed.

An isobutylene conversion product is discharged from the isobutylene conversion zone 80 by a line 82 leading to a methanol solvent extraction zone 100. The composition of a typical isobutylene conversion product may be as follows:

TABLE 4

| ISOBUTYLENE CONVERSION PRODUCT | |
|---|---|
| Component | % |
| Isobutylene | 5.4 |
| MTBE | 79.5 |
| Methanol | 12.2 |
| Dimethyl Ether | 1.6 |
| Other | 1.3 |

In accordance with the present invention, the isobutylene conversion product 82 is charged to a methanol solvent extraction zone 100 through the line 83 together with a MTBE recycle stream 210, obtained in a manner to be described, where it is countercurrently contacted with water introduced into the solvent extraction zone 100 by a charge line 102.

Within the methanol solvent extraction zone 100, solvent extraction conditions are established for countercurrent solvent extraction including a ratio of water to isobutylene conversion product within the range of about 0.1 to about 0.3 parts of water per part of isobutylene conversion product per hour, and more preferably include a ratio of water to isobutylene conversion product within the range of about 0.1 to about 0.2 parts of water per part of isobutylene conversion product per hour. Extraction conditions may suitably include a temperature of about 20° to about 60° C., and more preferably from about 30° to about 40° C., and a pressure of about 50 to about 500 psia, and more preferably from about 50 to about 150 psia.

As a consequence, a supernatant extract 60 will be formed which is withdrawn from the methanol solvent extraction zone 100 by line 110 leading to a MTBE purification distillation column 120. The raffinate 150 is discharged from the solvent extraction zone 100 by way of a bottoms discharge line 150 leading to a dimethyl ether recovery distillation column 160.

Within the methyl tertiary butyl ether purification distillation column 120, distillation conditions are established including a liquid reflux temperature of about 30° to about 60° C., and more preferably from about 40° to about 55° C., a reboiler temperature of about 100° to about 140° C., and more preferably from about 125° to about 135° C. and a pressure of about 70 to about 120 psia, and more preferably from about 90 to about 110 psia, to thereby form a second lower boiling (lighter) distillation fraction comprising isobutylene and water discharged from the second distillation column 120 by a line 140 and a second higher boiling (heavier) distillation fraction 130 consisting essentially of product, namely methyl tertiary butyl ether.

The second distillation fraction 140 will comprise a mixture of isobutylene and water and may be processed in any desired manner. For example, it may be charged to a decantation zone (not shown) where it can settle to form a supernatant isobutylene phase and a water phase. If desired, all or a part of the supernatant isobutylene phase may be recycled to the isobutylene conversion zone 80.

The raffinate 150 charged to the dimethyl ether recovery distillation zone 160 will comprise methyl tertiary butyl ether, methanol isobutylene, dimethyl ether, and water. For example, the composition of the raffinate 150 may be as follows:

TABLE 5

| EXTRACT | |
|---|---|
| Component | % |
| Isobutylene | 1.2 |
| MTBE | 7.2 |
| Methanol | 33.3 |
| Dimethyl Ether | 3.0 |
| Water | 54.4 |
| Other | 0.9 |

Although dimethyl ether has a specific gravity of only 0.661, a boiling point of −24.5° and a flash point of −42° C., as shown in the table, it remains dissolved in the heavier raffinate stream 150 rather than the lighter extract stream 110. Within the dimethyl ether recovery distillation column 160 distillation conditions are established, such as a reflux temperature of about 40° to about 70° C., and more preferably from about 55° to about 65° C., and a reboiler temperature of about 80° to about 120° C., and more preferably from about 105° to about 125° C., and a pressure of about 40 to about 45 psia to form a third lower boiling (lighter)

vaporized distillation fraction 170 comprising methyl tertiary butyl ether and a third higher boiling (heavier) distillation fraction 220 comprising water and methanol. For example, the composition of the overhead stream 110 and the bottoms stream 150 may be as follows:

TABLE 6

| Component | Overhead % | Bottoms % |
|---|---|---|
| Isobutylene | 8.0 | 0.0 |
| MTBE | 53.0 | 0.0 |
| Dimethyl Ether | 15.0 | 0.0 |
| Acetone | 2.0 | 0.0 |
| Methanol | 21.0 | 35.0 |
| Water | 0.2 | 64.0 |
| Other | 0.8 | 1.0 |

In accordance with the present invention, the vaporized overhead fraction 170 is passed through a suitable cooling means, such as a heat exchanger 172 where it is cooled to a liquefaction temperature of about 40° to about 70° C. and is then charged by line 174 to an accumulator or drum 180. The drum is maintained at a temperature of about 40° to about 80° C. (e.g., 50° C.) and a pressure of about 35 to about 45 psia (e.g., 38 psia). The drum 180 is provided with a rectifier 200 fitted with a throttling control valve 190 and a heat-exchange zone 202 which may suitably be maintained at a temperature of about −2° C. with a refrigerant such as propylene. During operations, the throttling valve 190 on the rectifier 200 is actuated so as to permit controlled vaporization of a portion of the liquified fraction 174 sufficient to permit all of the dissolved dimethyl ether to vaporize and pass into the rectifier. The vapors, after passing through the valve 190 are cooled to a temperature of about −5° to about 0° C. in the heat exchange zone 202, so that most of the vapors will liquify and drain back into the drum 180. However, all of the dimethyl ether and carbon monoxide and some of the isobutylene will be discharged from the rectifier 200 through the vent line 204.

As an example, about 1000 parts per hour of a raffinate having the composition shown in Table 5 may be fractionated in the column 160 to provide about 322 parts per hour of a vaporized overhead fraction 170 having the composition set forth in Table 6 and about 850 parts per hour of a bottoms fraction 220 having the composition set forth in Table 6. The vaporized overhead fraction 170, after partial liquefaction in the heat exchanger 172 is charged by line 174 to the drum 180. About 175 parts per hour of the partially liquified fraction 170 are returned to the column 160 as reflux and about 125 parts per hour of the liquified fraction 170 is returned by the line 210 to the methanol extraction zone 100. About 22 parts per hour of vapors are vented from the rectifier 200 through the vent line 204 and will comprise about 84 wt. % dimethyl ether, about 11 wt. % of isobutylene and about 5 wt. % other.

In accordance with the present invention the vapors in the line 204 are cooled to a liquefying temperature in heat exchanger 206 and then charged by a line 208 to distillation column 300 where they are separated into a lower boiling (lighter) distillation fraction 310 consisting essentially of dimethyl ether and a higher boiling (heavier) fraction 312 comprising isobutylene and dimethyl ether.

The higher boiling (heavier) fraction 312 suitably may be recycled to the line 210 leading to the methanol extraction zone 100.

The lower boiling (lighter) distillation fraction 310 suitably is passed through a heat exchanger 320 and then by line 322 to an accumulator or drum 324. From thence, the dimethyl ether is charged by a line 326 to a pump 328 for recycle to the distillation column 300 as reflux through reflux charge line 330 and for recovery as a purified dimethyl ether product through discharge line 340.

The third higher boiling (heavier) distillation fraction 220 is charged to a methanol distillation zone 230 where it is fractionated under distillation conditions which may suitably include a liquid reflux temperature of about 30° to about 80° C., and more preferably from about 60° to about 75° C., a reboiler temperature of about 100° to about 140° C., and more preferably from about 110° to about 120° C., and a pressure of about 15 to about 60 psia, and more preferably from about 20 to about 30 psia, into a lower boiling (lighter) methanol distillation fraction 34 which may be suitably charged to the line 36 to the tertiary butyl alcohol etherification reaction zone 40. A higher boiling (heavier) distillation fraction 240 consisting essentially of water is discharged from the fourth methanol distillation zone 230 by way of a line 240 and may be discharged from the system.

EXAMPLE

The invention will be further illustrated by the following specific example which is given by way of illustration, and not as a limitation on the scope of this invention. Where parts are mentioned, they are parts by weight.

In accordance with a preferred embodiment of the present invention, a tertiary butyl alcohol feedstock is continuously charged to the peroxides decomposition zone 20 by a line 10 where it is thermally treated under peroxide decomposition conditions including a temperature of about 100° to about 200° C., a pressure of about 80 to about 500 psia and a space velocity of about 0.5 to 4 volumes of feedstock per reactor volume per hour to thereby provide a substantially peroxides-free tertiary butyl alcohol product.

The peroxides-contaminated feedstock and substantially peroxides-free reaction product discharged from the peroxide decomposition zone 20 will typically have compositions as follows:

TABLE 7

PEROXIDE DECOMPOSITION ZONE FEED AND PRODUCT

| Component | Feed (Wt. %) | Product (Wt. %) |
|---|---|---|
| DTPB[1] | 0.87 | 0.02 |
| TBA[2] | 97.2 | 97.4 |
| Water | 0.1 | 0.02 |
| Other[3] | 1.8 | 2.6 |

[1]Ditertiary butyl peroxide
[2]Tertiary butyl alcohol
[3]Includes acetone, tertiary butyl formate isopropyl alcohol, etc.

The substantially peroxides-free tertiary butyl alcohol reaction product 30 is charged together with methanol from lines 32 and 34 to the tertiary butyl alcohol etherification reaction zone 40 in amounts such that about 2 moles of methanol are charged per mole of tertiary butyl alcohol.

Within the tertiary butyl alcohol etherification reaction zone 40, the feed mixture is passed through a bed of a suitable etherification catalyst such as Amberlyst 15 under reaction conditions, as described above, to provide a reaction product 50 having, for example, the following composition.

TABLE 8

ETHERIFICATION REACTION ZONE REACTION PRODUCT

| Component | Wt. % (Approx.) |
| --- | --- |
| Methanol | 2.8 |
| TBA | 14.5 |
| Water | 14.0 |
| Isobutylene | 3.0 |
| MTBE | 34.5 |
| Acetone | 0.4 |
| 2-Propanol | 6.0 |

The etherification zone reaction product is discharged from the etherification reaction zone 40 by a line 50 leading to primary methyl tertiary butyl ether distillation zone 60 where fraction 50 is separated into a first lower boiling (lighter) distillation fraction 70 comprising about 6.5 wt. % isobutylene, about 16.5 wt. % methanol and about 75 wt. % MTBE and a first higher boiling (heavier) fraction 90 comprising about 37 wt. % methanol, about 26.0 wt. % tertiary butyl alcohol, about 26 wt. % water, about 11 wt. % isopropanol and about 0.5 wt. % of other contaminants.

The first distillation fraction 70 is continuously charged to an isobutylene conversion zone 80 through the line 70 and brought into contact therein with a solid resin etherification catalyst, such as Amberlyst 15, under conversion conditions as described above to form an isobutylene conversion product which is discharged from the isobutylene reaction zone 80 by a line 82 and which has the following composition:

TABLE 9

ISOBUTYLENE CONVERSION PRODUCT

| Component | Feed | Product |
| --- | --- | --- |
| Isobutylene | 11 | 5.5 |
| MTBE | 71 | 80 |
| Methanol | 15 | 12 |
| Other[1] | 3 | 3 |

[1]Includes dimethyl ether acetone and 2-propanol

The isobutylene conversion product 82 and the recycle fraction 210 are continuously charged by way of a charge line 83 to the methanol extraction zone 100 in an amount such that the ratio of water to feedstock 83 is about 0.1 to about 0.3 part of water per part of feed mixture 83. Within the methanol extraction zone 100, there is provided an overhead extract fraction 110 comprising isobutylene and methyl tertiary butyl ether and a raffinate 150, such as a raffinate having the composition given in Table 5.

The extract is fed by a line 110 to a second methyl tertiary butyl ether purification distillation zone 120 where it is resolved by distillation into a second lower boiling (lighter) distillation fraction 140 comprising isobutylene and water and a second higher boiling (heavier) distillation fraction 130 consisting essentially of methyl tertiary butyl ether which is discharged as product.

Within the dimethyl ether recovery distillation column 160 the raffinate is resolved under distillation conditions as set forth above into a third lower boiling (lighter) distillation vaporized overhead fraction 170 comprising methyl tertiary butyl ether and a third higher boiling (heavier) distillation fraction 220 comprising water and methanol and having the composition set forth in Table 6.

In accordance with the present invention, the vaporized overhead fraction 170 is passed through a suitable cooling means, such as a heat exchanger 172 where it is liquified and then charged to a drum 180. The drum 180 is provided with a rectifier 200 fitted with a throttling control valve 190 and a heat-exchange zone 202. Controlled vaporization of a portion of the liquified fraction 174 is established sufficient to permit all of the dissolved dimethyl ether to vaporize and pass into the rectifier.

In accordance with the present invention the vapors in the line 204 are cooled to a liquefying temperature in heat exchanger 206 and then charged by a line 208 to distillation column 300 where they are separated into a lower boiling (lighter) distillation fraction 310 consisting essentially of dimethyl ether and a higher boiling (heavier) fraction 312 comprising isobutylene and dimethyl ether.

The higher boiling (heavier) fraction 312 suitably may be recycled to the line 210 leading to the methanol extraction zone 100.

The lower boiling (lighter) distillation fraction 310 suitably is passed through a heat exchanger 320 and then by line 322 to an accumulator or drum 324. From thence, the dimethyl ether is charged by a line 326 to a pump 328 for recycle to the distillation column 300 as reflux through reflux charge line 330 and for recovery as a purified dimethyl ether product through discharge line 340.

Having thus described my invention, what is claimed is:

1. In a method wherein methanol and isobutylene are reacted in the presence of a solid resin etherification catalyst to form a methyl tertiary butyl ether product stream containing contaminating quantities of dimethyl ether, methanol and isobutylene, the improvement for obtaining high purity dimethyl ether which comprises the steps of:

a) separating the methyl tertiary butyl ether product stream into a first lower boiling fraction comprising isobutylene and methyl tertiary butyl ether and a first higher boiling fraction comprising residual methyl tertiary butyl ether, methanol, dimethyl ether and water, b) charging the first higher boiling fraction to a first distillation column and separating it therein into a second lower boiling distillation fraction comprising methyl tertiary butyl ether, methanol, isobutylene, dimethyl ether, and water and a second higher boiling heavier distillation fraction comprising methanol and water, c) recovering dimethyl ether and isobutylene from the second lower boiling distillation fraction, and d) charging the recovered dimethyl ether and isobutylene to a second distillation column and separating it therein into a third lower boiling distillation fraction consisting essentially of dimethyl ether and a third higher boiling distillation fraction comprising dimethyl ether and isobutylene.

2. In a method wherein methanol and isobutylene are reacted in the presence of a solid resin etherification catalyst to convert isobutylene and methanol to methyl tertiary butyl ether and to form a methyl tertiary butyl ether product stream containing contaminating quantities of dimethyl ether, methanol and isobutylene, the improvement for obtaining high purity dimethyl ether which comprises the steps of:

a) continuously charging the methyl tertiary butyl ether product stream to a methanol solvent extraction zone and countercurrently contacting it therein with water to provide an extract comprising isobutylene and methyl tertiary butyl ether and a bottoms raffinate comprising residual methyl tertiary butyl ether, methanol, dimethyl ether and water, b) charging the extract to a first distillation column and separating it therein into a lower boiling distillation fraction comprising methyl tertiary butyl ether, methanol, isobutylene, dimethyl ether, and water and a higher boiling distillation fraction comprising methanol and water, c) charging the lower boiling distillation fraction, as a liquid, to an accumulator and venting from the drum a vapor by-product comprising dimethyl ether and isobutylene, d) liquefying the vented dimethyl ether and isobutylene, and e) charging the liquified dimethyl ether and isobutylene to a second distillation column and separating it therein into a lower boiling distillation fraction consisting essentially of dimethyl ether and a higher boiling distillation fraction comprising dimethyl ether and isobutylene.

3. A method which comprises the steps of:

a) continuously reacting methanol with tertiary butyl alcohol in a tertiary butyl alcohol etherification reaction zone containing a bed of an etherification catalyst to form a tertiary butyl alcohol reaction product comprising methanol, unreacted tertiary butyl alcohol, water, isobutylene and methyl tertiary butyl ether, b) continuously charging the tertiary butyl alcohol reaction product to a primary methyl tertiary butyl ether recovery distillation zone and separating it therein into a first lower boiling methanol and isobutylene-containing methyl tertiary butyl ether distillation fraction comprising methyl tertiary butyl ether, isobutylene and methanol and a first higher boiling distillation fraction comprising methanol, tertiary butyl alcohol and water, c) continuously charging the first lower boiling distillation fraction to an isobutylene conversion reaction zone and contacting it therein with a solid resin etherification catalyst to thereby convert isobutylene and methanol to methyl tertiary butyl ether and form a methyl tertiary butyl ether product stream containing contaminating quantities of dimethyl ether, methanol and isobutylene, d) continuously charging the methyl tertiary butyl ether product stream to a methanol solvent extraction zone and countercurrently contacting it therein with water to provide an extract comprising isobutylene and methyl tertiary butyl ether and a bottoms raffinate comprising residual methyl tertiary butyl ether, methanol, dimethyl ether and water, e) continuously charging the raffinate to a second methyl tertiary butyl ether purification distillation zone and separating it therein into a second lower boiling distillation fraction comprising isobutylene and water and a second higher boiling distillation fraction consisting essentially of methyl tertiary butyl ether, f) continuously charging the extract to a third methyl tertiary butyl ether distillation zone and separating it therein into a third lower boiling distillation fraction comprising methyl tertiary butyl ether, methanol, isobutylene, dimethyl ether, carbon monoxide and water and a third higher boiling distillation fraction comprising methanol and water, g) continuously charging the third higher boiling fraction to a fourth methanol recovery distillation zone and separating it therein into a fourth lower boiling distillation fraction comprising methanol and a fourth higher boiling distillation fraction comprising water, h) continuously charging the third lower boiling distillation fraction, as a liquid, to an accumulator, or drum, and venting from the drum a vapor by-product comprising dimethyl ether and isobutylene, and i) recycling the vented liquid third lower boiling distillation fraction to said methanol solvent extraction zone.

* * * * *